(12) United States Patent
Fuller et al.

(10) Patent No.: US 10,744,507 B2
(45) Date of Patent: Aug. 18, 2020

(54) SCREENING DEVICE FOR ANALYSIS OF BODILY FLUIDS

(71) Applicant: Premier Biotech, Inc., Minneapolis, MN (US)

(72) Inventors: Kevin S. Fuller, Chaska, MN (US); Wayde J. Altendorf, Hickson, ND (US)

(73) Assignee: Premier Biotech, Inc., Minneapolis, MN (US)

( * ) Notice: Subject to any disclaimer, the term of this patent is extended or adjusted under 35 U.S.C. 154(b) by 146 days.

(21) Appl. No.: 16/008,720

(22) Filed: Jun. 14, 2018

(65) Prior Publication Data

US 2019/0015829 A1 Jan. 17, 2019

Related U.S. Application Data

(63) Continuation of application No. 14/834,534, filed on Aug. 25, 2015, now abandoned, which is a continuation of application No. 14/079,558, filed on Nov. 13, 2013, now abandoned.

(60) Provisional application No. 61/725,898, filed on Nov. 13, 2012.

(51) Int. Cl.
*B01L 3/00* (2006.01)
*G01N 1/18* (2006.01)
*A61B 10/00* (2006.01)

(52) U.S. Cl.
CPC .......... *B01L 3/508* (2013.01); *A61B 10/0051* (2013.01); *B01L 3/5029* (2013.01); *G01N 1/18* (2013.01); *B01L 2200/026* (2013.01); *B01L 2200/0605* (2013.01); *B01L 2300/042* (2013.01); *B01L 2300/0618* (2013.01); *B01L 2300/0663* (2013.01); *B01L 2300/0672* (2013.01); *B01L 2300/0832* (2013.01); *B01L 2300/0864* (2013.01)

(58) Field of Classification Search
CPC .. B01L 3/508; B01L 3/5029; B01L 2300/042; B01L 2200/0605; B01L 2300/0864; B01L 2300/0832; B01L 2300/0672; B01L 2300/0663; B01L 2300/0618; B01L 2200/026; G01N 1/18; A61B 10/0051
See application file for complete search history.

(56) References Cited

U.S. PATENT DOCUMENTS

| | | |
|---|---|---|
| 3,849,256 A | 11/1974 | Linder |
| 5,186,897 A | 2/1993 | Eason et al. |
| 5,238,652 A | 8/1993 | Sun et al. |
| 5,869,003 A | 2/1999 | Nason |

(Continued)

FOREIGN PATENT DOCUMENTS

EP 0520408 12/1992

*Primary Examiner* — Samuel P Siefke
(74) *Attorney, Agent, or Firm* — Jiangqiong Liu (57) ABSTRACT

A screening device for testing saliva for the presence of certain constituents. The device has a D-shaped profile when viewed from above and includes a first wall with planar front face through which all of the test strips are viewed and a curved rear second wall. The device also includes a floor surface with an uppermost portion extending from the rear wall to a lowermost portion at the first wall such that saliva squeezed from a sampler at a location between the uppermost portion and the lowermost portion flows downwardly to the test strips.

20 Claims, 6 Drawing Sheets

(56) References Cited

U.S. PATENT DOCUMENTS

| | | | |
|---|---|---|---|
| 5,976,895 | A | 11/1999 | Cipkowski |
| 6,372,575 | B1 | 4/2002 | Lee et al. |
| 6,464,939 | B1 | 10/2002 | Bachand et al. |
| 6,488,669 | B1 * | 12/2002 | Sagona ................ B01L 3/508 600/584 |
| 6,497,843 | B2 | 12/2002 | Tydings |
| 6,548,019 | B1 | 4/2003 | Lee et al. |
| 6,616,893 | B1 | 9/2003 | Pham |
| 7,270,959 | B2 | 9/2007 | Hudak |
| 7,695,953 | B2 | 4/2010 | Gould et al. |
| 7,741,103 | B2 | 6/2010 | Guirguis |
| 7,837,939 | B2 | 11/2010 | Tung et al. |
| 7,879,623 | B2 | 2/2011 | Guirguis |
| 7,927,562 | B2 | 4/2011 | Wan et al. |
| 8,163,253 | B1 | 4/2012 | Hartselle |
| 8,940,527 | B2 | 1/2015 | Guirguis |
| 9,414,813 | B2 | 8/2016 | Engel et al. |
| 2003/0021727 | A1 | 1/2003 | Weyker et al. |
| 2003/0064526 | A1 | 4/2003 | Niedbala et al. |
| 2004/0184954 | A1 | 9/2004 | Guo et al. |
| 2005/0119589 | A1 | 6/2005 | Tung et al. |
| 2005/0202568 | A1 | 9/2005 | Tung et al. |
| 2006/0127274 | A1 | 6/2006 | Vallejo et al. |
| 2008/0166820 | A1 | 7/2008 | Gould et al. |
| 2009/0117665 | A1 | 5/2009 | Tung et al. |
| 2012/0021375 | A1 | 1/2012 | Binner et al. |
| 2012/0046574 | A1 | 2/2012 | Skakoon |
| 2012/0282681 | A1 | 11/2012 | Teixeira et al. |
| 2013/0280698 | A1 | 10/2013 | Propper et al. |

\* cited by examiner

SCREENING DEVICE FOR ANALYSIS OF BODILY FLUIDS

RELATED APPLICATIONS

This application is a continuation of U.S. patent application Ser. No. 14/834,534, filed Aug. 25, 2015, which is a continuation of U.S. patent application Ser. No. 14/079,558, filed Nov. 13, 2013, which claims the benefit of U.S. Provisional Patent Application No. 61/725,898, filed Nov. 13, 2012, the disclosures of which are incorporated by reference herein in their entireties.

FIELD OF THE INVENTION

This application is directed generally to devices and methods for analysis of the presence of constituents in fluids, and more specifically to devices and methods for analysis of the presence of constituents in bodily fluids for drug test screening.

BACKGROUND OF THE INVENTION

Various drug screening devices are known for testing a sample of bodily fluids for the presence of certain constituents. These devices typically include a container for receiving a bodily fluid from a delivery device, and a plurality of reagent test strips arranged to contact the bodily fluid, with each test strip being sensitive to a particular constituent of interest. The targeted constituents for screening can range from controlled substances such as alcohol and marijuana to illegal substances such as cocaine and methamphetamines.

For screening purposes, it is desirable to test for as many constituents as possible with a single sample, so as to reduce the nuisance factor associated with obtaining multiple bodily fluid samples. This is particularly a problem with saliva where sufficient quantitaties fro multiple tests is problematic. Accordingly, many devices are intended to distribute the sampled bodily fluid among as many test strips as reasonably possible. This is typically accomplished by arranging a plurality of test strips on each of several sides of the container.

Problems associated with a plurality of test strips arrayed on several sides of a test container include maldistribution of bodily fluid samples to the various test strips and the necessity to inspect more than one side of the container to determine the screening result. A screening device that addresses these maladies would be welcomed.

SUMMARY OF THE INVENTION

Various embodiments of the invention include a device and method for adequately distributing a sample of bodily fluid among a plurality of test strips and preventing maldistribution of sampled fluid that can lead to an invalid test result, all while displaying the test results on a single face of the screening device. Certain embodiments also enable a slight and passive pressurization of a sampling chamber to augment the wicking or capillary action of the sampled fluid along the test strips.

One problem with the prior art arrangement of having a plurality of test strips arrayed on several sides of a test container is that the arrangement is prone to operator error. Persons conducting the screening test often hold the screening device in their hand while awaiting the test results. While holding the device, there is a tendency to tilt the proximal face of the device backward for easier reading. Unfortunately, this can cause the bodily fluid under test to pool at the bottom of the distal face of the testing device, thus starving the test strips that are disposed on the proximal face. The result is an invalid test for the constituents represented by the test strips on the proximal face.

Structurally, various embodiments of the invention include a container or cup having a first or "viewing" side through which all of the test strips can be viewed. The bottom of the cup is inclined and intersects the viewing side along a junction line that constitutes the lowest portion of the cavity within the cup where the bodily fluid collects. The test strips are oriented so that the detection end proximate the junction line for in contact with the bodily fluid that collects at the low portion of the cavity. By this arrangement, all of the test strips can be inspected by viewing a single surface of the cup, and the inclined surface of the bottom of the cup directs all of the bodily fluid into contact with the detection end of the test strips. Furthermore, the angle of the intersection between the bottom and the viewing side can be steep enough to counter a substantial holding angle induced by the operator.

In certain embodiments, a three-dimensional gasket is implemented to provide certain sealing and pressurization advantages. The three-dimensional gasket can be made of a soft, pliable material to provide a sealing surface between the gasket and the cup and to provide a seal between a sampling stem that is inserted through the gasket. The pliable material can also cause the three-dimensional gasket to act as a diaphragm; when the sampling stem is inserted into the three-dimensional gasket, the displaced air causes the three-dimensional gasket to expand (as would a diaphragm), thereby causing the air contained by the three-dimensional gasket to become slightly pressurized. The pressurization can assist in the diffusion of the bodily fluid into the test strips, thus augmenting the capillary action between the bodily fluid and the test strip.

The device can also provide barriers between the detection ends of adjacent test strips to prevent more absorbent or faster absorbing test strips from drawing test fluid away from less absorbent or slower absorbing test strips.

A feature and advantage of embodiments of the invention is a specimen sampling device for saliva where the saliva is absorbed in a sponge, is squeezed into a saliva pathway of a specimen container, the saliva pathway is pressurized urging the saliva into engagement with a plurality of sample test strips. In embodiments a vent may be provided downstream of where the saliva engages the test strips. In embodiments, the plurality of test strips are each positioned in a plurality of recesses in a row, the recesses having an overfill level whereby fluid that overflows one recess flows into an adjacent recess. In embodiments, the pressurization may be provided by a stem attached to the sponge, the stem having a sliding plunger member. In embodiments the pressurization may be provided by a separate manual squeeze or push pump as part of the specimen sampling device.

Another feature and advantage of embodiments of the invention is a specimen sampling device for saliva where the saliva is absorbed in a sponge, is squeezed into a saliva pathway of a specimen container, the saliva pathway leading to a plurality of sample test strips aligned in a linear row of at least 8 strips positioned on a substantially planar wall and exposed to be readable through one or more transparent regions, the strips having a sample receiving end that is placed at the bottom of an inclined plate in the saliva pathway. In some such embodiments, embodiments may have a gasket sealingly enclosing a specimen chamber including the inclined plate and a row of recesses into which the at least 8 strips extend. In some such embodiments, a curved, wall is positioned opposite the planar wall.

An additional feature and advantage of embodiments of the invention is a specimen sampling device for saliva where the saliva is absorbed in a sponge, is squeezed into a saliva pathway of a specimen container, the saliva pathway leading to a plurality of sample test reservoirs, each with test strip extending therein, a gasket with a separate aperture for each respective test strip, the gasket providing sealing between the saliva pathway including and the reservoirs and regions of the container above the saliva pathway thereby preventing unintended migration of the saliva upward.

DETAILED DESCRIPTION

Figure 1:
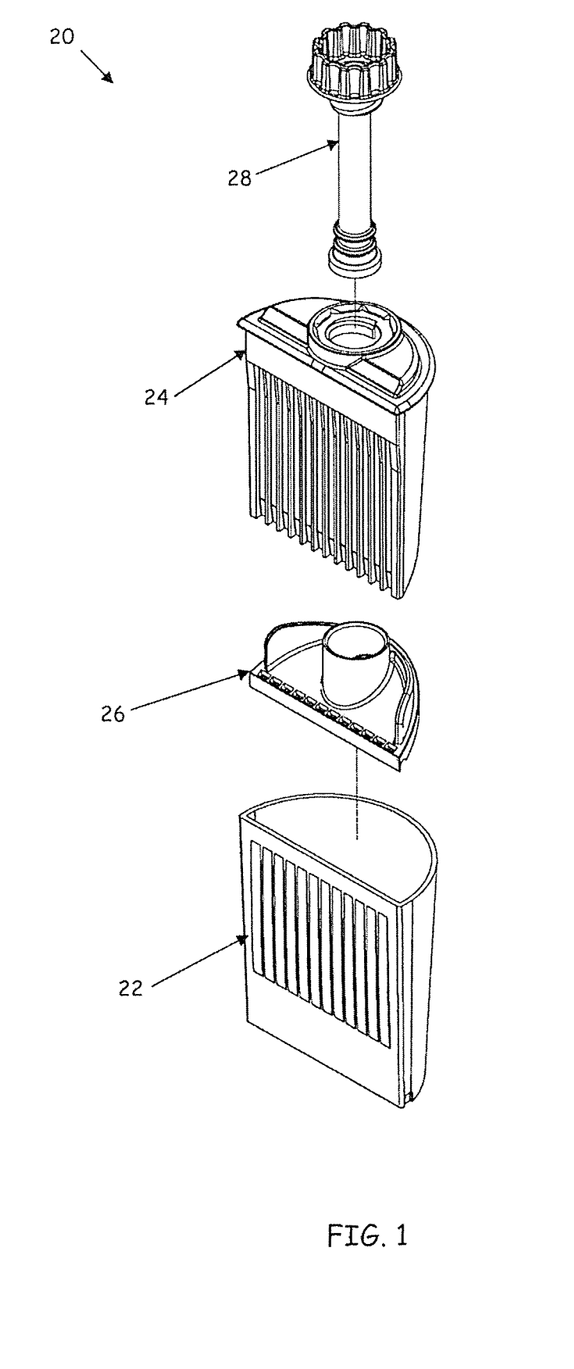
FIG. 1 is an exploded view of a testing assembly for screening of bodily fluids in an embodiment of the invention.

Referring to FIG. 1, a testing assembly 20 for screening bodily fluids for the presence of certain constituents is depicted in an embodiment of the invention. The screening device includes a container or cup 22, a test strip and sampling stem holder 24 (hereinafter "holder 24"), a three-dimensional gasket 26 and a sampling stem 28.

Figure 2:
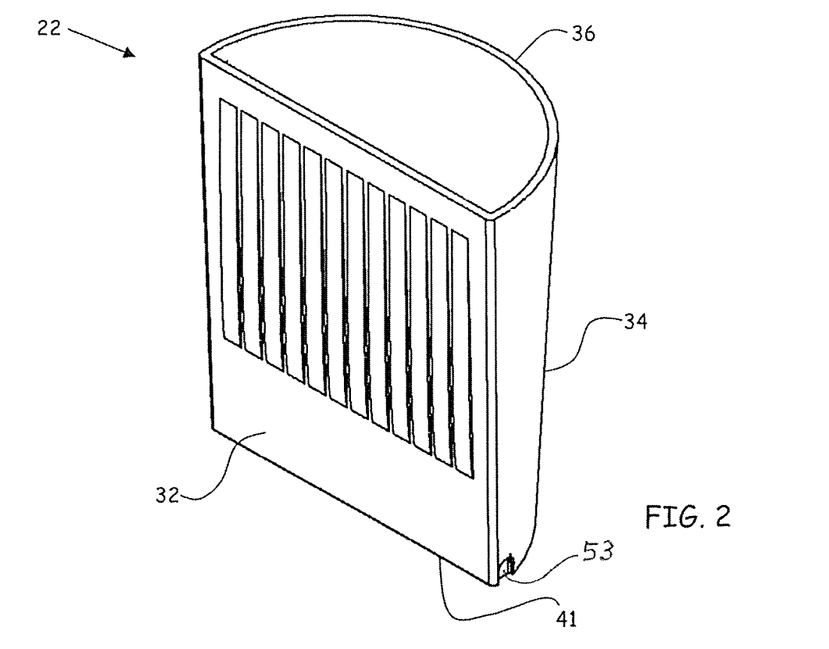
FIG. 2 is a perspective view of a cup of the testing assembly of FIG. 1 in an embodiment of the invention.
Figure 3:
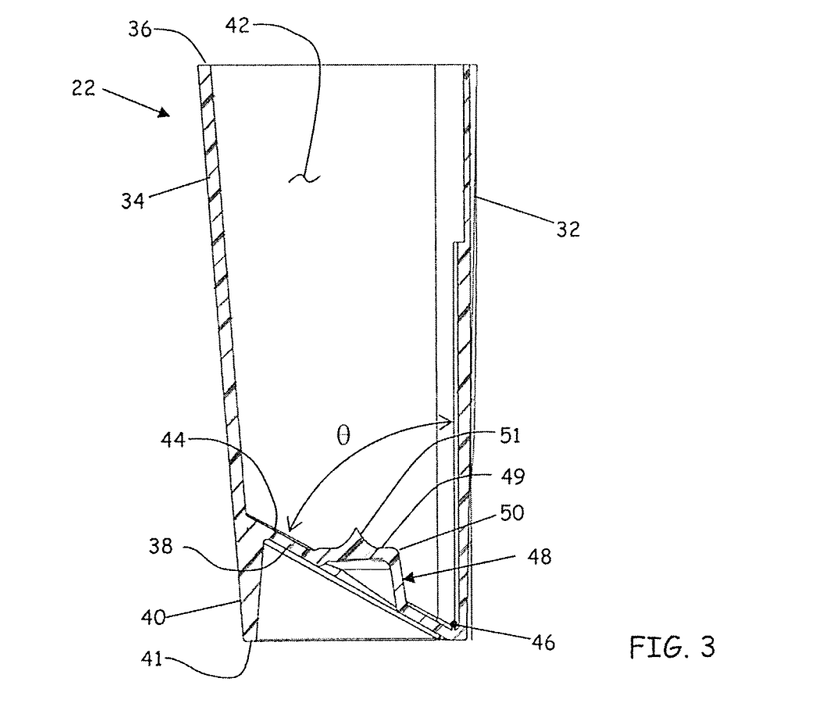
FIG. 3 is a sectional view of the cup of FIG. 2.

Referring to FIGS. 2 and 3, the cup 22 is depicted in isolation in an embodiment of the invention. The cup 22 includes a plurality of sides 32 and 34 that extend upward from a containment bottom 38 to form a continuous upper edge 36, the sides 32, 34 and containment bottom 38 defining a cavity 42. The sides 32 and 34 can also extend below the containment bottom 38 to establish a base portion 40 with a lower edge 41 registers the testing assembly 20 in an upright position. A first of the sides (side 32 in FIGS. 2 and 3) can be substantially planar. In one embodiment, the containment bottom 38 defines an inclined surface 44 that intersects the plurality of sides 32 and 34. The inclined surface 44 intersects the first side 32 along a junction line 46, defining an acute angle θ between the first side 32 and the inclined surface 44. The junction line 46 is the lowermost extremity of the cavity 42 when the cup 22 is in the upright position.

While the inclined surface 44 is depicted as being substantially planar, it is noted that the inclined surface 44 is not limited to a planar configuration. For example, the inclined surface could also be convex, with a steeper slope at the junction line 46 than at other locations on the inclined surface. Alternatively, the inclined surface could be concave, with a more gradual slope at the junction line 46 than at other locations.

In one embodiment, the containment bottom 38 can further include a pedestal portion 48 that extends from the inclined surface 44 into the cavity 42. The pedestal portion 48 can include a top face 49 having a perimeter 50. A securing structure 51, such as a point or barb (as depicted in FIG. 3), can be included on or as part of the top face 49 of the pedestal portion.

Various embodiments of the cup 22 can also include a syringe access port 53 located proximate a lower corner of the cup 22. The syringe access port comprises a region where the thickness of the cup 22 is thinned to enable manual puncturing with a syringe.

The cup 22 can be fabricated from a variety of materials available to the artisan, including but not limited to polycarbonate, styrene-butadiene copolymers (SBCs) such as K-RESIN, and clear styrene.

Figure 4:
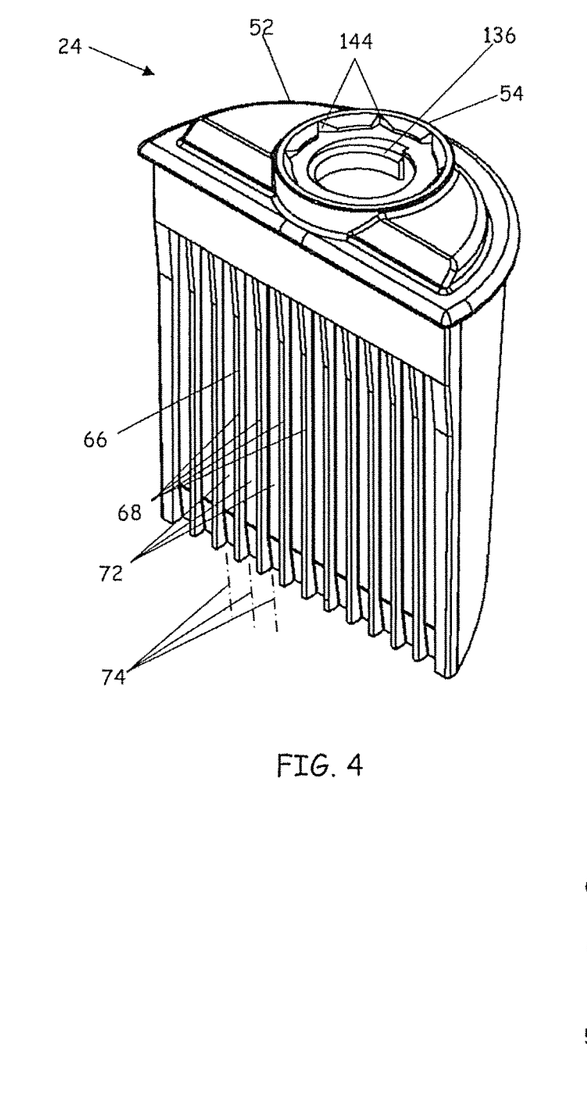
FIG. 4 is a perspective view of a test strip and sampling stem holder of FIG. 1 in an embodiment of the invention.
Figure 5:
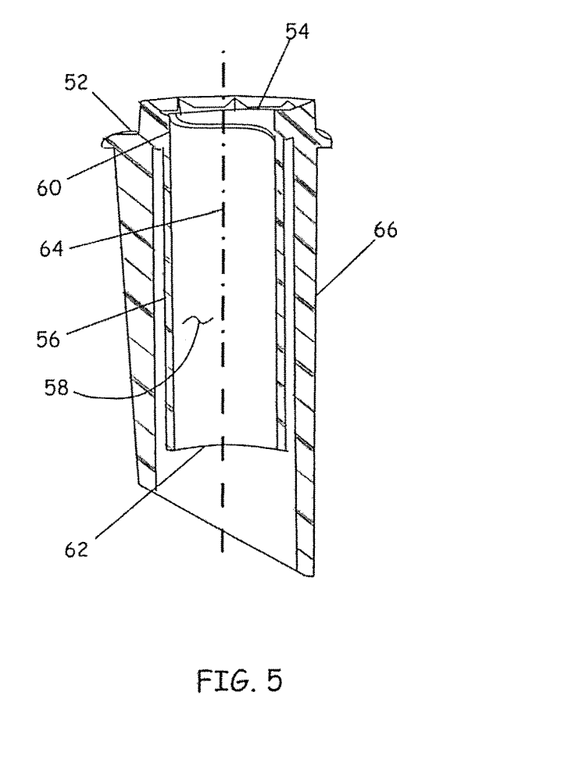
FIG. 5 is a side sectional view of the holder of FIG. 4.

Referring to FIGS. 4 and 5, the holder 24 is depicted in isolation in an embodiment of the invention. The holder 24 includes a cap portion 52 having an access port 54 formed therein. The holder 24 also includes a through passage structure 56 that defines a through passage 58 that passes through the holder 24. The through passage structure 56 includes a proximal end 60 and a distal end 62, each being concentric about an insertion axis 64. The proximal end 60 of the through passage structure 56 includes the access port 54. The through passage structure 56 can comprise a hollow tube that depends from the cap portion 52 (as depicted), or a bore that extends through a substantially solid holder 24.

The holder 24 also includes a planar face 66 that extends downward from the cap portion 52. The planar face 66 includes a plurality of parallel ribs 68 that define a plurality of elongate channels 72. The elongate channels 72 each define a channel axis 74.

The holder 24 can be fabricated from a variety of materials available to the artisan, including but not limited to polycarbonate, styrene and acrylonitrile butadiene styrene (ABS).

Figure 6:
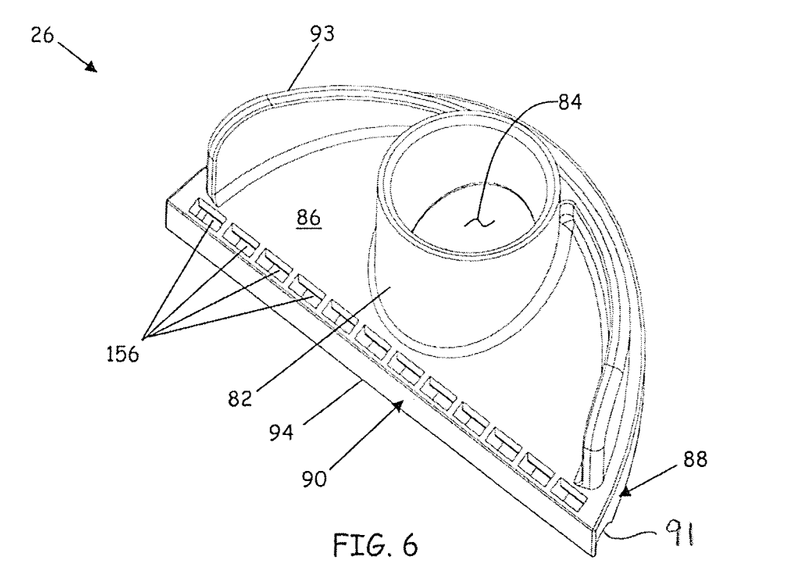
FIG. 6 is a perspective view of the top of a three-dimensional gasket of FIG. 1 in an embodiment of the invention.
Figure 7:
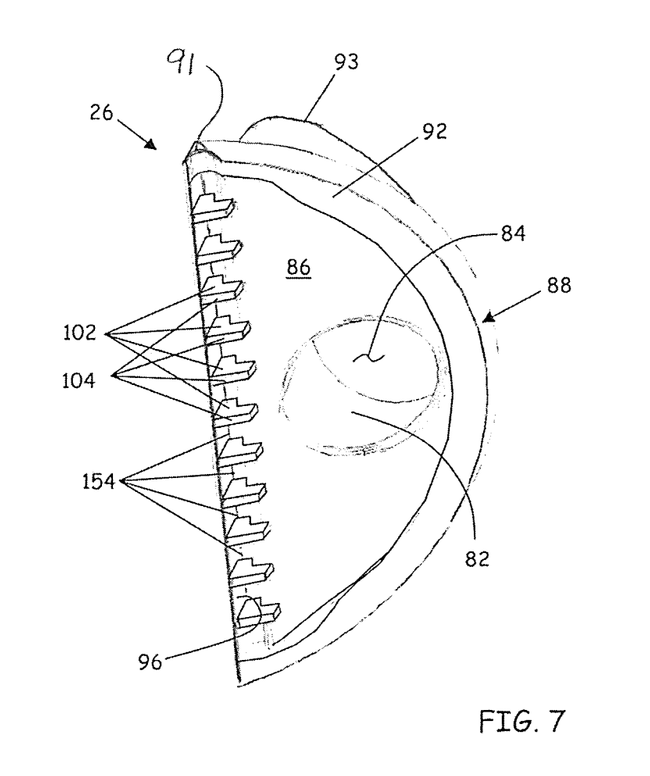
FIG. 7 is a perspective view of the bottom of the three-dimensional gasket of FIG. 6.

Referring to FIGS. 6 and 7, the three-dimensional gasket 26 is depicted in an embodiment of the invention. The three-dimensional gasket 26 includes a passage extension structure 82 that defines an extended passage 84 and a diaphragm portion 86 that depends from and extends radially outward from the passage extension structure 82. A perimeter structure 88 of the three-dimensional gasket 26 surrounds and depends from the diaphragm portion 86, the perimeter structure 88 having a lower face 92 that extends below the diaphragm portion 86. The three-dimensional gasket can also include a notch 91 that, upon assembly, aligns with the syringe access port 53 of the cup, enabling easy access to the chamber 150. The three-dimensional gasket 26 can also include guide tabs 93 that assist in guiding, registering and seating the three-dimensional gasket into the holder 24 during assembly.

The perimeter structure 88 includes a front portion 90 having an outer face 94 and an inner face 96. The outer face 94 is adapted to contact an inner surface of the first side 32 of the cup 22. In one embodiment, the inner face 96 includes a plurality of riblets 102 that extend inwardly, in the general direction of the extended passage 84. The riblets 102 can include lower surfaces 104 configured to engage the inclined surface 44 of the containment bottom 38. In one embodiment, the three-dimensional gasket 26 is fabricated from a soft, pliable material such as polyvinylchloride (PVC) or neoprene.

Figure 8:
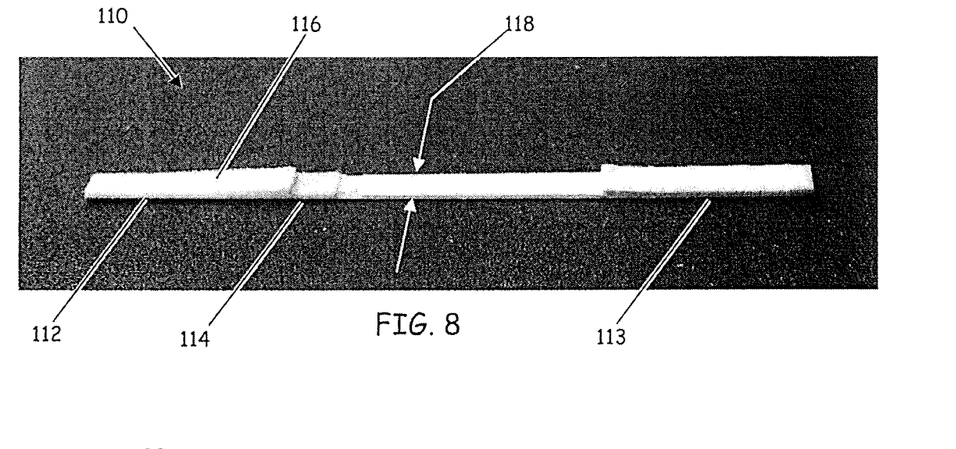
FIG. 8 is a perspective view of a test strip.

Referring to FIG. 8, a test strip 110 is depicted. The test strip 110 includes a detection end 112 and a non-detection end 113. The detection end 112 wicks fluid to a sensing zone 114 via capillary action through an absorbent material 116. The sensing zone 114 is configured with reagents that react and provide a visual indication when a certain constituent is present in the bodily fluid. A width 118 of the test strip 110 is dimensioned to slidingly engage a corresponding one of the elongate channels 72. In the depicted embodiment, the test strip 110 is characterized as having increased thickness at both the detection and non-detection ends 112 and 113 due to the presence of the absorbent material 116.

Figure 9:
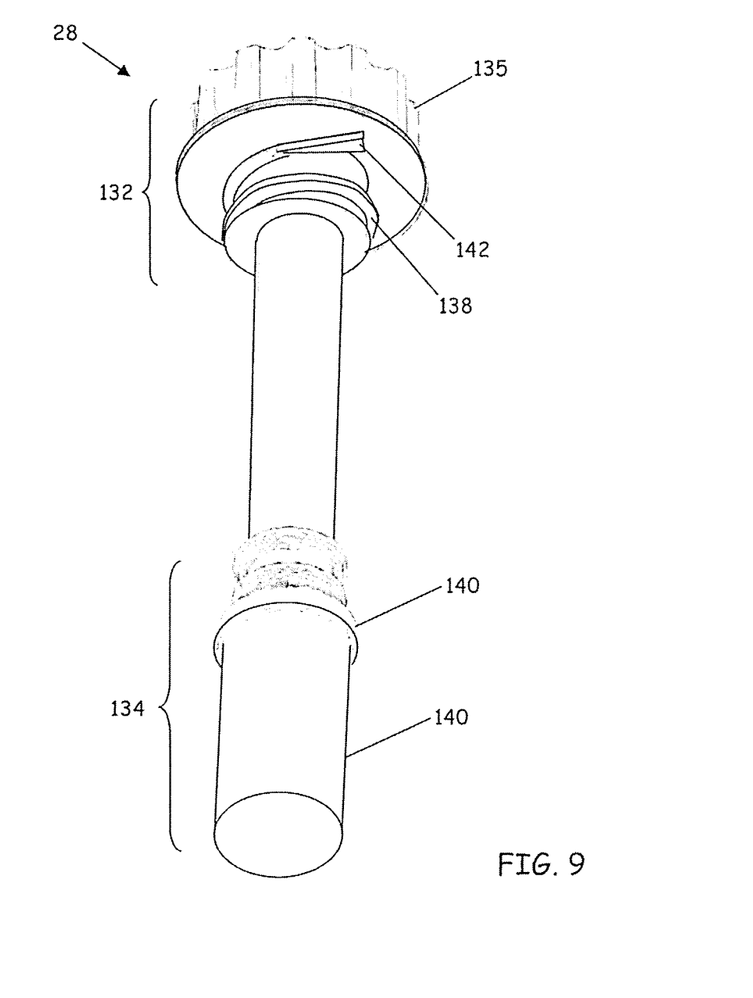
FIG. 9 is a perspective view of a sampling stem of FIG. 1 in an embodiment of the invention.

Referring to FIG. 9, the sampling stem 28 is depicted in an embodiment of the invention. The sampling stem 28 is characterized as having a proximal portion 132 and a distal portion 134. The proximal portion 132 can include a handle or knob 135 for handling and manipulation of the sampling stem 28. Certain aspects of the sampling stem 28 are depicted and described at U.S. Patent Application Publication No. 2012/0094303 to Engel et al., which is hereby incorporated by reference herein except for express definitions contained therein. The sampling stem 28 can be fabricated from a variety of materials available to the artisan, including but not limited to polycarbonate, styrene-butadiene copolymers (SBCs) such as K-RESIN, and clear styrene.

In one embodiment, the proximal portion 132 includes structure that is complementary with structure on the cap portion 52 for securing the sampling stem 28 in a fixed position along the insertion axis 64 relative to the cap portion 52. In the depicted embodiment, the complementary structures comprise a female threaded structure 136 proximate the access port 54 of the cap portion 52 of the holder 24 and a male threaded portion 138 proximate the proximal portion 132 of the sampling stem 28. Other complementary structures could also be utilized, including a detent-and-groove snap fit structure a bayonet-style lock or a clasp.

In one embodiment, the sampling stem 28 and the access port 54 are configured to provide a ratchet-and-pawl mechanism for rotationally locking the sampling stem 28 relative to the holder 24. In the depicted embodiment, the sampling stem 28 includes a pawl 142 distal to the male threaded portion 138. The pawl 142 is configured to engage ratchet notches 144 (FIG. 4).

The distal portion 134 of the sampling stem 28 includes a sampling swab 140 that is mounted to a collar 141. In one embodiment, the collar 141 is comprised of a transparent material to enable ultraviolet activation of bonding agents that are placed between the sampling swab 140 and the collar 141. The distal portion 134 is configured for insertion through the through passage 58 and extended passage 84. In one embodiment, the collar 141 is sized to provide a sliding seal between the collar 141 and the extended passage 84. Also, in one embodiment, the through passage 58 as well as the extended passage 84 is tapered (i.e., has a larger diameter at the proximal end than at the distal end) in order to guide the distal portion 134 without causing it to bind, but still affecting a seal as the collar 141 approaches its final axial location along the insertion axis 64.

Figure 10:
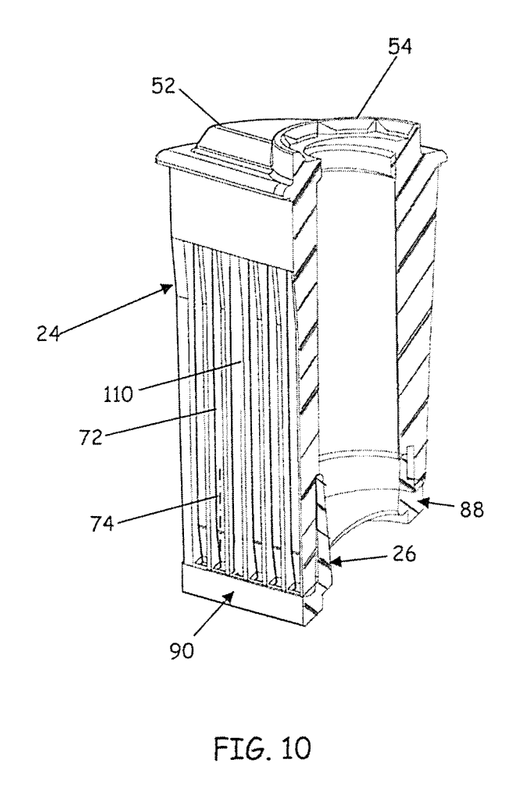
FIG. 10 is a perspective cutaway view of the holder and three-dimensional gasket of FIG. 1 in assembly.
Figure 11:
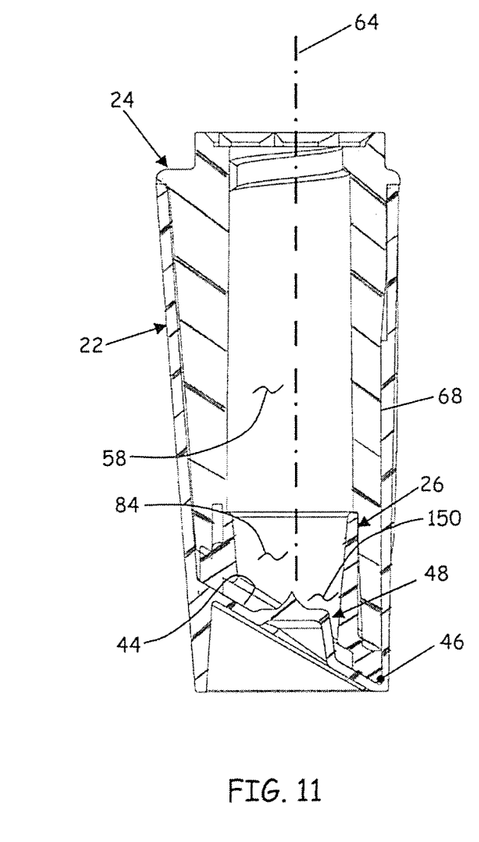
FIG. 11 is a sectional view of the cup, holder and three-dimensional gasket of FIG. 1 in assembly.
Figure 12:
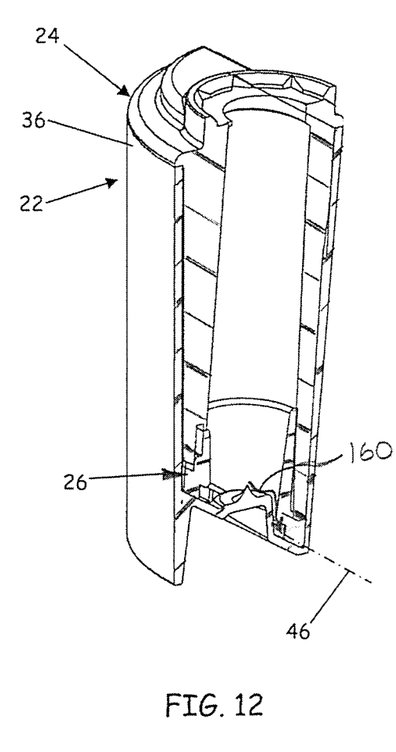
FIG. 12 is a perspective cutaway view of the cup, holder and three-dimensional gasket of FIG. 1 in assembly.

Referring to FIGS. 10 through 12, the testing assembly 20 is depicted in various states of assembly. In assembly, the three-dimensional gasket 26 is coupled to the bottom of the holder 24 and the test strips inserted into the respective elongate channels 72 so that the detection end extends into the extended channel. The holder 24 and three-dimensional gasket 26 assembly, with test strips 110 loaded in the channels 72, is inserted into the cup 22 such that the three-dimensional gasket 26 is disposed between the holder 24 and the containment bottom 38. The cap portion 52 of the holder 24 is brought into contact with and joined to the continuous upper edge 36 of the cup 22 (FIG. 12). Any joining or bonding method available to the artisan can be utilized to join the cap portion 52 to the cup 22, including gluing, fusion or sonic welding, or a detent-and-groove snap fit engagement.

After assembly, the orientation of the elongate channels 72 of the holder 24 are such that the channel axes 74 are substantially perpendicular to the junction line 46. The extended passage 84 is in substantial alignment with the through passage 58 and is substantially concentric about the insertion axis 64. The pedestal portion 48 can extend partway into the extended passage 84. The perimeter 50 of the top face 49 of the pedestal portion 48 can be normal to the insertion axis 64, and can also be concentric about the insertion axis 64.

The three-dimensional gasket 26 can be compressed between the holder 24 and the inclined surface 44 of the containment bottom 38 such that the lower face 92 of the perimeter structure 88 is in sealing contact with the inclined surface 44 of the containment bottom 38. The outer face 94 of the front portion 90 of the perimeter structure 88 can also be in sealing contact with the interior of the first side 32 of the cup 22 just above the junction line 46. In this way, a chamber 150 is defined, bounded by the diaphragm portion 86, the perimeter structure 88 and the inclined surface 44. The chamber 150 is accessible via the extended passage 84.

Each of the riblets 102 of the three-dimensional gasket 26 extend into the chamber 150 and are in substantial alignment with a corresponding one of the ribs 68 of the planar face 66 of the holder 24 to form a plurality of channel extensions 152. Engagement of the lower surfaces 104 of the riblets 102 with the inclined surface 44 creates a plurality of pockets 154 (partially depicted in FIG. 7) that are proximate the junction line 46. In one embodiment, the detection end 112 of a given strip 110 accesses the channel extensions 152 and pockets 154 through slots 156 (FIG. 6) formed proximate the front portion 90 of the perimeter structure 88 of the three-dimensional gasket 26. The slots 156 can be dimensioned so that the absorbent material 116 of the detection end 112 of an occupying test strip 110 is in light contact with the interior of the slot 156. During assembly, the light contact between the test strip 110 and the slot 156 can be enough to hold the test strip 110 in its respective elongate channel 72 until the assembly operation is complete.

In operation, the sampling swab 140 of the sampling stem 28 is saturated with bodily fluid to be analyzed (e.g., saliva from a person being screened for drug use). The distal portion 134 of the sampling stem 28 is then inserted into the access port 54 and slid through the through passage 58 of the holder 24 and into the extended passage 84 of the three-dimensional gasket 26. The sampling swab 140 is thereby brought into contact with the pedestal portion 48. The sampling stem 28 is further pushed into the access port 54 until the male threaded portion 138 of the sampling stem 28 is engageable with the female threaded structure 136 of the access port 54 (or other complementary coupling structures become engageable). The male threaded portion 138 is then threaded into the female threaded structure 136 until the proximal portion 132 of the sampling stem 28 is fully engaged within the access port 54 (e.g., by registration of the knob 135 against an upper periphery of the access port 54).

For embodiments utilizing the ratchet-and-pawl mechanism, the threading action (rotation of the sampling stem 130) causes the pawl 142 to engage with the ratchet notches 144. This prevents the sampling stem 28 from rotating out of the access port 154, thus locking the sampling stem 28 in a fixed axial position along the insertion axis 64.

The threading action between the proximal portion 132 and the access port 54 also causes the sampling swab 140 to be further extended into the extended passage 84 of the three-dimensional gasket 26, causing the sampling swab 140 to be compressed against the pedestal portion 48 (when present) or, more generally, against the containment bottom 38. The securing structure 51 secures the sampling swab 140, thereby inhibiting the swab 140 from sliding laterally relative to the insertion axis 64. By securing the sampling swab 140, more efficient extraction of bodily fluid from the sampling swab 140 is attained during compression.

The compression acts to wring the bodily fluid out of the sampling swab 140, which then flows over the pedestal portion 48, down the inclined surface 44 and along saliva pathways 160 (FIG. 12) to pool along the inner face 96 of the perimeter structure 88 proximate the lower most portion of the cavity 42, i.e., into the pockets 154 located proximate the junction line 46). The pockets 154 that are nearest the center of the three-dimensional gasket 26 (i.e., more proximate the insertion axis 64) will tend to receive more fluid initially than the pockets 154 located near the extreme corners of the three-dimensional gasket 26. The riblets 102 can be dimensioned so that the pockets 154 accept only an amount needed to adequately activate the corresponding test strip 110. Accordingly, as the bodily fluid flows into the nearest of the pockets 154, these pockets will overflow and cascade over the riblets 102 as the pockets 154 become successively filled. Given an ample quantity of bodily fluid, all of the pockets 154 should receive sufficient bodily fluid for analysis. In one embodiment, the riblets 102 are sized and spaced so that a dozen pockets 154 can hold 1 ml of fluid and the sampling swab 140 sized to accept 20 ml of bodily fluid.

The depicted embodiments present twelve elongate channels 72 for housing twelve test strips 110; however, configurations having more or less channels 72 can also be implemented, depending on the quantity of fluid available for analysis. Typically, the number of elongate channels 72 ranges from 6 to 15.

While the cascading action between the pockets 154 can take several seconds, the absorption by the test strips 110 is on the order of minutes. Therefore, the riblets 102 prevent more absorbent or faster absorbing test strips from drawing test fluid away from less absorbent or slower absorbing test strips, thus providing better and more predictable analysis results.

The insertion of the distal portion 134 of the sampling stem 28 into the extended passage 84 also acts to pressurize the chamber. The three dimensional gasket 26 can be made of a soft, pliable material, so that the perimeter structure 88 provides a seal with the inclined surface 44, and a seal is also affected between the collar 141 and the extended passage 84 as the collar 141 of the sampling stem 28 reaches its final position within the extended passage 84. Thus, as the distal portion 134 of the sampling stem 28 moves into its final position, air is displaced and pushed into the chamber 150. The pliable material can also cause the diaphragm portion 86 to flex, thereby causing the air contained by the three-dimensional gasket 26 to become slightly pressurized. While some venting may occur between these sealed surfaces, as well as through the absorbent material 116 deposited in the slots 152, the pressurization can still assist in the diffusion of the bodily fluid into the absorbent material 116, thus augmenting the capillary action between the bodily fluid and the test strip 110.

All of the features disclosed in this specification (including any accompanying claims, abstract and drawings), and/or all of the steps of any method or process so disclosed, can be combined in any combination, except combinations where at least some of such features and/or steps are mutually exclusive.

Each feature disclosed in this specification (including any accompanying claims, abstract and drawings) can be replaced by alternative features serving the same, equivalent or similar purpose, unless expressly stated otherwise. Thus, unless expressly stated otherwise, each feature disclosed is one example only of a generic series of equivalent or similar features.

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. A device for testing saliva, the device comprising:
a cup comprising an outer planar forward wall connecting to an outer curved rearward wall providing a D-shaped outer perimeter of the device when viewed from below and above, the outer planar forward wall providing the straight portion of the "D" and the outer curved rearward wall providing the remainder of the "D", the cup having a lower edge that registers the cup in an upright position, a single inclined plate traversing continuously upwardly and rearwardly between the planar forward wall and the curved rearward wall, the inclined plate having a lowermost portion of the plate proximate the planar front wall and an uppermost portion of the inclined plate exclusively at the rearward wall and the inclined plate defining a cavity with a single lowermost extremity of the cavity positioned at the planar forward wall;
a holder including a cap portion;
the cap portion positioned at a top portion of the cup, the cap portion having a D-shaped outer perimeter when viewed from above, the D-shaped outer perimeter providing an outermost periphery of the device when viewed from above; wherein the cap portion comprising a through passage structure comprising a hollow tube positioned below the cap portion, the hollow tube extending toward the inclined plate; and wherein the holder includes a planar face that extends downward from the cap portion into the cup and the planar face comprises a plurality of parallel ribs that define a plurality of elongate channels for engaging a test strip;
a sampling stem having a proximal portion and a distal portion, the distal portion including a sampling swab for absorbing saliva, the sampling stem insertable through the cap into the through passage structure whereby the swab engages an upwardly facing surface for compressing the sampling swab at the upwardly facing surface to squeeze saliva in the sampling swab out of the sampling swab, the upwardly facing surface at a location forward of and below the uppermost portion of the inclined plate.

2. The device for testing saliva of claim 1, wherein the test strip holder has a wall extending downwardly from the cap portion that conforms to and follows the D-shaped outer perimeter of the device and extends toward the inclined plate, the wall having a planar face positioned at the planar forward wall.

3. The device for testing saliva of claim 1, wherein the sampling stem further comprises a female threaded portion to cooperate with a male threaded portion on the cap portion.

4. The device for testing saliva of claim 3, wherein the sampling stem and the cap portion have a ratchet and pawl mechanism for locking the sampling stem on the cap portion.

5. The device for testing saliva of claim 1, wherein the inclined plate has a pedestal portion for contacting the sampling swab and the upwardly facing surface is on the pedestal portion.

6. The device for testing saliva of claim 2, wherein planar face including a plurality of riblets, said plurality of riblets defining a plurality of channel extensions on said inner face of said planar face for receiving the test strips.

7. The device for testing saliva of claim 1, wherein the inclined plate has a substantially planar upwardly facing surface extending from the rearward wall to the lowermost portion.

8. A device for testing saliva, the device comprising:
a cup comprising a planar forward wall connecting to a curved rearward wall defining a D-shaped outer wall perimeter when viewed from above and below, a single inclined plate traversing and extending upwardly and rearwardly between the planar forward wall and connecting to the curved rearward wall at an uppermost portion of the inclined plate, the inclined plate having a planar upper surface and an inclination extending the entire distance from the forward wall to the rearward wall, the forward wall, the curved rearward wall, and the inclined plate defining a single cavity having a single lowermost extremity along the planar front wall, the inclined plate and planar forward wall defining an acute angle, wherein the forward wall has a side to side width and the forward side to side width is a maximum side to side width of the cup;
a holder having a planar face adjacent the planar forward wall, comprising a cap portion positioned at the opening of the cup, the cap portion having through passage structure comprising a hollow tube, the hollow tube extending toward the inclined plate; the planar face of the holder positioned in the cavity adjacent the planar forward wall of said cup, a plurality of test strips positioned between the planar face and the planar forward wall; wherein the cap portion is positioned at a top portion of the cup, the cap portion has a D-shaped outer perimeter when viewed from above, and the D-shaped outer perimeter provides an outer most periphery of the device when viewed from above;
a sampling stem having a proximal portion and a distal portion, the distal portion including a sampling swab for absorbing saliva, the sampling stem insertable into the through passage structure of the cup for squeezing out the saliva at a location below the uppermost portion of the inclined plate.

9. The device for testing saliva of claim 8, wherein the holder has a wall extending downwardly from the cap portion that conforms to and follows the D-shaped outer perimeter of the device and extends toward the inclined plate, the wall having the face adjacent the forward wall.

10. The device for testing saliva of claim 9, wherein the sampling stem and the cap portion have a ratchet and pawl mechanism for locking the sampling stem on the cap portion.

11. The device for testing saliva of claim 8, wherein the inclined plate has a pedestal portion for contacting the sampling swab.

12. The device for testing saliva of claim 8, further comprising a three dimension gasket within said cavity of said cup between said holder and the inclined plate.

13. The device for testing saliva of claim 8, wherein the planar face of the holder includes a plurality of riblets, said plurality of riblets defining a plurality of channel extensions on said inner face of said planar face for receiving the test strips.

14. The device for testing saliva of claim 8, wherein the cup has a lower edge that registers the device in an upright position.

15. A device for testing saliva, the device comprising:
a cup comprising a planar forward wall connecting to a curved rearward wall defining a D-shaped opening and a D-shaped outer perimeter at a top of the cup when viewed from above and below, a containment bottom that includes a single inclined surface that intersects the planar forward wall and the curved rearward wall and defining a cavity with a single lowermost extremity of the cavity at the juncture line of the inclined surface and the planar forward wall, the inclined surface having an uppermost portion at the rearward wall;
a plurality of test strips positioned at the forward wall and each of the plurality of test strips extending to the single lowermost extremity of the cavity, all test strips of the device positioned at the planar forward wall;
a D-shaped cap portion positioned at the opening of the cup, the cap portion having through passage structure comprising a hollow tube, the hollow tube extending toward the inclined plate, the D-shaped cap portion welded or glued to the cup for sealing the D-shaped opening of the cup;
a sampling stem having a proximal portion and a distal portion, the distal portion including a sampling swab for absorbing saliva, the sampling stem insertable into the through passage structure and being attachable to the cap portion, the device having an upwardly facing surface for compressing saliva out of the sampling swab, the upwardly facing surface positioned below the uppermost portion of the inclined surface.

16. The device for testing saliva of claim 15, wherein the cup has a thinned region for puncturing with a syringe, the thinned region positioned proximate the containment bottom.

17. The device for testing saliva of claim 15, wherein the planar face and the cap portion are part of a holder and the planar face extends from the cap portion.

18. The device for testing saliva of claim 15 wherein the sampling stem further comprises a female threaded portion to cooperate with a male threaded portion on the cap portion.

19. The device for testing saliva of claim 18 wherein the inclined surface has a pedestal portion for contacting the sampling swab.

20. The device of claim 15, wherein the forward wall has a side to side width that defines a maximum side to side width of the cup.

* * * * *